US007238377B2

(12) United States Patent
Piccirilli et al.

(10) Patent No.: US 7,238,377 B2
(45) Date of Patent: Jul. 3, 2007

(54) USE OF AN OIL OF THE GOURD FAMILY FOR INHIBITING 5 ALPHA-REDUCTASE ACTIVITY

(75) Inventors: Antoine Piccirilli, Versailles (FR); Jacqueline Smadja, Sainte Clothilde (FR); Philippe Msika, Paris (FR); Isabelle Grondin, Sainte Clothilde (FR); Nathalie Piccardi, Egreve (FR)

(73) Assignee: Laboratoires Expanscience, Courbevoie (FR)

( * ) Notice: Subject to any disclaimer, the term of this patent is extended or adjusted under 35 U.S.C. 154(b) by 70 days.

(21) Appl. No.: 10/482,280

(22) PCT Filed: Jul. 1, 2002

(86) PCT No.: PCT/FR02/02277

§ 371 (c)(1),
(2), (4) Date: Dec. 29, 2003

(87) PCT Pub. No.: WO03/002088

PCT Pub. Date: Jan. 9, 2003

(65) Prior Publication Data

US 2004/0234632 A1 Nov. 25, 2004

(30) Foreign Application Priority Data

Jun. 29, 2001 (FR) .................................. 01 08648

(51) Int. Cl.
*A61K 36/00* (2006.01)
(52) U.S. Cl. ....................... 424/776; 424/725; 424/401
(58) Field of Classification Search ..................... None
See application file for complete search history.

(56) References Cited

U.S. PATENT DOCUMENTS

| 3,881,000 | A | * | 4/1975 | Freidmann et al. .......... 514/105 |
| 4,677,123 | A | * | 6/1987 | Shroot et al. ................ 514/680 |
| 6,183,747 | B1 | * | 2/2001 | Ren ........................... 424/758 |

FOREIGN PATENT DOCUMENTS

| DE | 41 11 569 A | 10/1992 |
| EP | 0 359 196 | 3/1990 |
| JP | 52 051033 A | 4/1977 |
| JP | 62 093214 A | 4/1987 |
| JP | 04 036215 A | 2/1992 |
| WO | WO 87 05019 A | 8/1987 |
| WO | 44 29 747 A | 2/1996 |
| WO | WO 01 05416 A | 1/2001 |

OTHER PUBLICATIONS

Tandon et al., "Study of Cucumis Melo Momordica Seed Oil", J. Indian Chem. Soc., vol. 53, No. 11, Nov. 1976; pp. 1161-1162.
Armougom et al., "Composition en acides gras des extraits lipidiques de quelques graines de cucurbitacees tropicales," Oleagineux Corps Gras Lipides, vol. 5, No. 4, Jul. 1998, pp. 323-328.
ABSTRACT: Caplus, Chemical Abstracts Service, Columbus, Ohio, US, Data: Accession No. 1989:72545 XP002196408.
ABSTRACT: Caplus, Chemical Abstracts Service, Columbus, Ohio, US, Data: Accession No. 1999:416742 XP002196409.
ABSTRACT: Caplus, Chemical Abstracts Service, Columbus, Ohio, US, Data: Accession No. 1992:262300 XP002196410.
Database WPI Week 197722; Derwent Publications Ltd., London, GB; AN 1977-39162y, XP002196411.
Database WPI: Week 198722, Derwent Publications Ltd., London, GB, AN 1987-154858, XP002196412.

* cited by examiner

*Primary Examiner*—Susan Hoffman
(74) *Attorney, Agent, or Firm*—Foley & Lardner LLP

(57) ABSTRACT

The invention concerns the use of at least an oil derived from the seeds of the gourd family selected from the group consisting of *Lagenaria*, *Luffa* and *Momordica*, for preparing a composition designed to inhibit 5α-reductase activity, and the use of said oil for preparing a composition for treating prostatic hypertrophy, prostatic adenoma, acne, hyperseborrhea, alopecia, and hirsutism. The invention also concerns cosmetic treatment methods, in particular for greasy skin. The invention further concerns the use of at least an oil derived from seeds of the gourd family in a nutritional food composition for humans and/or animals as additive for inhibiting 5α reductase activity.

11 Claims, No Drawings

USE OF AN OIL OF THE GOURD FAMILY FOR INHIBITING 5 ALPHA-REDUCTASE ACTIVITY

The present invention relates to the use of at least one oil from seeds of members of the gourd family chosen from the group consisting of *Lagenaria, Luffa* and *Momordica*, for preparing a composition intended to inhibit 5α-reductase activity, and also to the use of such an oil for preparing a composition intended for the treatment of prostatic hypertrophy, prostatic adenoma, acne, hyperseborrhea, alopecia and hirsutism. The invention also relates to methods of cosmetic treatment, in particular of greasy skin. The invention also relates to the use of at least one oil from seeds of members of the gourd family, in a foodstuff for humans and/or animals as an additive for inhibiting 5α-reductase activity.

Tropical members of the gourd family belonging to the three genera *Lagenaria, Luffa* and *Momordica* are crop plants in particular on Réunion Island or in India. Among these tropical members of the gourd family, mention may in particular be made of long, "pitted" and bottle gourds (*Lagenaria leucaritha*), angled luffa (*Luffa acutangula*), smooth luffa (*Luffa cylindrica*) and balsam pear (*Momordica charantia*).

Gourds of the genus *Lagenaria leucaritha* are plants generally grown in Asia, in particular in China or in Japan. They are also found in areas surrounding the Indian Ocean. These plants are annual herbaceous plants from 8 to 10 meters high. Pollination of their flowers produces cylindrical fruits, swollen at their base, called gourds. Three types of gourds of the genus *Lagenaria leucaritha*, long, "pitted" and bottle gourds, are for example found on Réunion Island. These fleshy fruits contain, at their center, flat and elongated seeds exhibiting a lipid content of between 12 and 25% by weight.

Luffas belonging to the genera *Luffa cylindrica* and *Luffa acutangula*, respectively of the smooth or angled type, originate from India. They are annual herbaceous plants consisting of rampant stems which can reach up to 5 meters in length.

The fruits contain black, oval seeds the lipid content of which is between 20 and 30% by weight.

Balsam pair of the genus *Momordica charantia* originates from India, but is also grown on Réunion Island. It is an annual herbaceous plant which can produce creepers 2 meters long and the green-colored oblong fruits of which contain flat seeds. The lipid content of these seeds is approximately 30% by weight.

Tropical members of the gourd family such as *Luffa cylindrica* have already been used in cosmetic applications, but the oil extracted from the seeds of these members of the gourd family, containing the total lipids of these seeds, has never been used in cosmetic formulations. Thus, patent application EP 359 196 describes cosmetic formulations for treating the skin, comprising at least one adjuvant and from 1 to 90% by weight of an extract of *luffa cylindrica*, the extract being an aqueous or alcoholic extract obtained, for example, by percolation.

The applicant has thus discovered, surprisingly, that the oil extracted from the seeds of tropical members of the gourd family, advantageously chosen from the group consisting of *Lagenaria leucaritha, Luffa acutangula, Luffa cylindrica* and *Momordica charantia*, can be used in a cosmetic composition, advantageously administered in an external topical manner, intended to inhibit 5α-reductase activity and to act in particular on greasy or shiny skin or hair, on skin with a tendency toward acne, on areas of the scalp affected by alopecia of nonpathological origin or on areas of the skin which are very hairy.

In addition, the oils extracted from the seeds of tropical members of the gourd family are found to be cosmetically acceptable compounds which are nonaggressive for the skin, nontoxic and hypoallergenic.

The applicant has also discovered, surprisingly, that the oil extracted from the seeds of tropical members of the gourd family according to the present invention can be used in a pharmaceutical or food composition intended to inhibit 5α-reductase activity.

5α-reductase is an NADPH-dependant microsomal enzyme which exists in the form of two isoenzymes synthesized from two different genes.

The type 1 isoenzyme of 5α-reductase is found essentially in the liver and skin, more particularly in the sebaceous glands of the non-genital skin and of the scalp, and appears at puberty. The type 2 isoenzyme is dominant in the prostate and in the skin of the differentiated sexual areas: genital region, beard, and plays a role in sexual differentiation. The distribution of the type 1 and 2 isoenzymes of 5α-reductase in the skin and the skin appendages in humans can be illustrated in table 1 below.

TABLE 1

Distribution of the type 1 and 2 isoenzymes of 5α-reductase in the skin and the skin appendages in humans

|  |  | H5-αr1 | H5-αr2 |
|---|---|---|---|
| EPIDERMIS | Basal layer | ++ | + |
|  | Spiny layer | + | ++ |
|  | Granular layer | + | − |
|  | Cornified layer | − | − |
| DERMIS | Fibroblasts | ++ | − |
| SEBACEOUS GLANDS | Basal cells | ++ | + |
|  | Glandular cells | ++ | − |
| ECCRINE SWEAT GLANDS | Excretory duct | − | − |
|  | Secretory cells | ++ | − |
|  | Myoepithelial cells | ++ | + |
| HAIR FOLLICLE | Dermal papilla | + | +? |
|  | Matrix cells | ++ | + |
|  | Inner epithelial sheath | ± | +++ |
|  | Outer epithelial sheath | ++ | − |
|  | Arrector muscle | + | − |

A certain number of pathological conditions exist for which a congenital or acquired exaggeration of the 5α-reductase activity is entirely or mainly responsible for the problems observed.

For example, in humans, this 5α-reductase enzyme, which is mainly located in the genital tissues and in the skin, catalyzes the hydroxylation of testosterone to 5α-reductase dihydrotestosterone (DHT). Now, since DHT is an androgen which is much more active than testosterone (approximately twice as active), the effects of the latter are amplified in the tissues where the DHT is produced. Too high a 5α-reductase activity thus leads to contents of androgen in the form of DHT which are too high in the prostate, hence an overstimulation of the latter resulting in undesirable growth which can lead to the pathological condition prostatic hypertrophy, or even to prostatic adenoma, most commonly requiring surgical intervention.

Other pathological conditions, of the dermatological type, can be observed in men or women as resulting from an overactivity of 5α-reductase, namely, in particular, acne, hirsutism or else alopecia.

In the skin, the 5α-reductase activity is greater in the sebaceous gland than in the other structures. Moreover, the seborrheic glands show 5α-reductase activity which is greater than those of the other areas of the skin. Consequently, the physiological level of sebaceous secretion appears to be closely related to the activity of this enzyme.

In individuals with acne, there is hyperactivity of 5α-reductase. Rather than an increase in serum androgen levels, it is an increase in precursors of DHT, the main factor of sebaceous function, which contribute to acne.

Greasy (or seborrheic) skin, besides its unsightly appearance, constitutes an area in which complications can occur. It affects the areas where there are many sebaceous glands and results mainly from androgenic overstimulation of sebaceous production by these specific glands. Hyperseborrhea contributes to the occurrence of common acne lesions.

In the scalp, the type 1 isoenzyme of 5α-reductase is found, in the sebaceous glands, and also in the hair follicle. The type 2 isoenzyme of 5α-reductase is located mainly in the inner epithelial sheath, and also in the dermal papilla of the hair. However, the latter localization remains to be specified.

Androgenic alopecia, the physiopathogenesis of which is very similar to that of acne, is the most common form of alopecia and without doubt that where there is the highest therapeutic demand. 5α-reductase appears to play an essential role in this pathological condition. In fact, men suffering from a genetic deficiency in the type 2 isoenzyme of 5α-reductase do not develop androgenetic alopecia.

Given the above, research has turned toward the development of 5α-reductase inhibitors. Certain steroids, such as progesterone, have been tested for this purpose, but the rapid metabolizing of this steroid makes it ineffective in vivo. In order to be active, the 5α-reductase inhibitor-must- -be sufficiently stable to block the activity of the enzyme in vitro. Finasteride, a steroidal competitive inhibitor, satisfies this condition, but it is more active on the type 2 isoenzyme than on the type 1 isoenzyme, and these two isoenzymes are only 50% homologous over the sequence of their amino acids. It is therefore especially in benign hyperplasia of the prostate that finasteride has already been tested.

Moreover, extract of *Serenoa Repens* is also known, as reference as a 5α-reductase inhibitor, extract of *Serenoa Repens* having the advantage, compared to finasteride, of being of natural origin as a plant extract which allows better comparison for test products also of natural origin. *Serenoa Repens*, also known under the name *Sabal serrulatum*, is a small palm tree which can be found in the United States (Florida), in North Africa and in Spain.

The applicant has now found, entirely surprisingly and unexpectedly, that use of the oil extracted from seeds of members of the gourd family chosen from the group consisting of *Lagenaria, Luffa* and *Momordica* makes it possible to obtain a notable effect of inhibition of 5α-reductase activity, thus in particular providing a novel response for the treatment of the dermatological pathological conditions and/or disorders mentioned above. The oil according to the present invention may thus be incorporated into a pharmaceutical composition, into a food product or into a food supplement, or else into a cosmetic composition.

A subject of the present invention is thus the use of at least one oil from seeds of members of the gourd family chosen from the group consisting of *Lagenaria, Luffa* and *Momordica*, advantageously *Lagenaria leucaritha, Luffa acutangula, Luffa cylindrica* and *Momordica charantia*, for preparing a composition intended to inhibit 5α-reductase activity.

The use of the oil from seeds of members of the gourd family for preparing a composition according to the present invention intended to inhibit the type 1 isoenzyme and/or the type 2 isoenzyme of 5α-reductase is particularly advantageous according to the present invention.

According to the present invention, the composition is advantageously intended for external topical use. It may, moreover, contain a cosmetically acceptable carrier.

The composition which is advantageously used according to the present invention may be in all the galenic forms usually used for external topical application. Advantageously according to the present invention, the composition is in the form of an aqueous, aqueous-alcoholic or oily solution, of an oil-in-water or water-in-oil or multiple emulsion, of an aqueous or oily gel, of an anhydrous liquid, pasty or solid product, or of a dispersion of oil in an aqueous phase by means of spherules, the spherules possibly being polymeric nanoparticles such as nanospheres and nanocapsules or, better still, lipid vesicles of the ionic and/or nonionic type. The composition may be more or less fluid, and may be in the form of a white or colored cream, an ointment, a milk, a lotion, a salve, a serum, a paste, a mousse, an aerosol or a stick.

The composition used according to the present invention may, moreover, contain the adjuvants which are usual in the cosmetics field, such as hydrophilic or lipophilic gelling agents, hydrophilic or lipophilic active agents, preserving agents, antioxidants, solvents, fragrances, fillers, screening agents, pigments, chelating agents, odor absorbers and dyestuffs. The amounts of these various adjuvants are those conventionally used in cosmetics and, for example, from 0.01% to 20% by weight, relative to the total weight of the composition. Depending on their nature, these adjuvants may be introduced into the fatty phase, into the aqueous phase, into the lipid vesicles and/or into the nanoparticles.

When the composition according to the present invention is an emulsion, the proportion of the fatty phase may range from 5% to 80% by weight, and preferably from 5% to 50% by weight, relative to the total weight of the composition. The oils, the emulsifiers and the coemulsifiers used in the composition in the form of an emulsion are chosen from those conventionally used in the field under consideration. The emulsifier and the coemulsifier are present in the composition in a proportion ranging from 0.3% to 30% by weight, and preferably from 0.5% to 20% by weight, relative to the total weight of the composition.

Among the oils which can be used according to the present invention, mention may in particular be made of mineral oils, other oils of plant origin (apricot oil, sunflower oil, plum oil), oils of animal origin, synthetic oils, silicone oils and fluoro oils (perfluoropolyethers). Fatty alcohols, such as cetyl alcohol, fatty acids or waxes, such as beeswax, can also be used as fatty substances according to the present invention.

Among the emulsifiers and coemulsifiers which can be used according to the present invention, mention may in particular be made of esters of fatty acid and of polyethylene glycol, such as PEG-40 stearate or PEG-100 stearate, esters of fatty acid and of polyol, such as glyceryl stearate and sorbitan tristearate.

Among the hydrophilic gelling agents which can be used according to the present invention, mention may in particular be made of carboxyvinyl polymers (carbomer), acrylic copolymers, such as copolymers of acrylate/alkyl acrylate, polyacrylamides, polysaccharides, natural gums and clays. Among the lipophilic gelling agents, mention may in particular be made of modified clays such as bentones, metal salts of fatty acids, hydrophobic silica and polyethylenes.

Advantageous according to the present invention, the composition also contains at least one compound chosen from the group consisting of hydrophilic active agents, lipophilic active agents, agents for modulating the differentiation, and/or proliferation and/or pigmentation of the skin, antibacterial agents, agents for modulating bacterial adhesion to the skin and/or mucous membranes, antifungal agents, calmatives, antipruriginous agents, keratolytic agents, free-radical scavengers, antiseborrheic agents, antidandruff agents, agents exhibiting anti-acne activity, anti-irritants, moisturizers, vitamins, anti-inflammatory agents, UVA and UVB screening agents, matting agents, light-reflecting pigments, anti-wrinkle active agents, anti-glycation agents, heat shock protein modulators and enzyme inhibitors.

Among the hydrophilic active agents which can be used according to the present invention, mention may in particular be made of proteins or protein hydrolysates, peptides such as peptides of lupin, amino acids, polyols, urea, allantoin, sugars and their derivatives, water-soluble vitamins, plant extracts and hydroxy acids.

Among the lipophilic active agents which can be used according to the present invention, mention may in particular be made of retinol (vitamin A) and derivatives thereof, tocopherol (vitamin E) and derivatives thereof, essential fatty acids, ceramides, essential oils, and salicylic acid and derivatives thereof.

The composition used according to the present invention may also contain other active agents intended in particular for the prevention and/or for the treatment of skin ailments. Among these active agents, mention may in particular be made of agents for modulating the differentiation and/or proliferation and/or pigmentation of the skin, such as retinoic acid and isomers thereof, retinol and esters thereof, vitamin D and derivatives thereof, phytoestrogens and kojic acid; antibacterial agents such as octanediol and conventional preserving agents (quaternary ammonium, etc.); agents for modulating bacterial adhesion to the skin and/or mucous membranes, such as certain sugar derivatives; antifungal agents, in particular compounds belonging to the imidazole class or salts thereof, compounds of the allylamine family, glycine derivatives (sodium hydroxymethylglycinate for example), piroctone olamine or else octopirox; calmatives such as salicylic acid, lupeol, allantoin, cornflower water, silanediol salicylate, derivatives of liquorice and enexolone.

Among the active agents intended in particular for the prevention and/or for the treatment of skin ailments which are optionally present in the composition according to the present invention, mention may also be made of: antipruriginous agents such as glycine; keratolytic agents such as alpha- and beta-hydroxy-carboxylic acids or beta-ketocarboxylic acids, or their salts, amides or esters, and more particularly hydroxy acids such as glycolic acid, lactic acid, salicylic acid, citric acid and, in general, fruit acids; free-radical scavengers, such as alpha-tocopherol or esters thereof, carotenoids, isoflavones, OPCs, flavonoids, superoxide dismutases, certain metal-chelating agents or ascorbic acid and esters thereof; antiseborrheic agents such as retinoids, sabal, extract of *Pygeum Africanum*, or zinc salts.

It is also possible to add to the composition according to the present invention, as active agents intended in particular for the prevention and/or for the treatment of skin ailments, antidandruff agents such as octopirox, zinc pyrithione or piroctone olamine; agents exhibiting anti-acne activity, such as retinoids, retinol, retinaldehyde, vitamins PP, benzoyl peroxides, erythromycin; anti-irritants such as thermal spring waters, polysaccharides, in particular anti-irritants with respect to irritant compounds possibly present in the compositions of the present invention; moisturizers such as polyols (for example glycerol); vitamins (for example D-panthenol or vitamins C, D, B6); anti-inflammatory agents such as thermal spring waters, polysaccharides; UVA and UVB screening agents of the organic and inorganic screen type; matting agents and light-reflecting pigments such as mixtures of titanium and mica; anti-wrinkle active agents such as retinol and derivatives thereof (retinaldehyde); anti-glycation agents; heat shock protein modulators; and enzyme inhibitors.

In a particular embodiment according to the present invention, the oil from seeds of members of the gourd family can be obtained according to the process consisting in extracting the total lipids from the seeds of members of the gourd family, dried and ground beforehand, using a solvent for the oils, and then in evaporating off the solvent.

The seeds of members of the gourd family according to the present invention are ground, for example, using a cylinder mill or a hammer mill. The solvent for the oils, used to extract the total lipids from the seeds forming the oil, is a conventional organic solvent for lipid extraction. The solvent is advantageously chosen from the group consisting of aliphatic alkanes, aromatic alkanes, aliphatic alcohols and their halogenated derivatives. Even more advantageously according to the present invention, the organic solvent is hexane. The extraction of the total lipids from the seeds of members of the gourd family is advantageously carried out by soxhlet extraction, which is technology well known to those skilled in the art. After extraction of the lipids contained in the seeds of members of the gourd family according to the present invention, the organic solvent is evaporated off, preferably by evaporation under vacuum.

In another particular embodiment according to the present invention, the oil from the seeds of members of the gourd family can be obtained according to the process consisting in extracting the lipids from the seeds of members of the gourd family by mechanical pressing of the seeds under cold conditions, advantageously by means of a continuous screw press, so as to produce, after filtration, first-press virgin oils.

The oils of members of the gourd family according to the present invention can be used crude or refined. For the purpose of the present invention, the term "refining" is intended to mean the unitary operations for purifying lipids of plant origin which are well known to those skilled in the art, among which mention may in particular be made of chemical neutralization, demucilating, decolorizing, deodorizing and winterization.

Advantageously according to the present invention, the oil extracted from the seeds of members of the gourd family is present at a concentration of between 0.01 and 95%, preferably between 0.1 and 30% by weight, relative to the total weight of the composition.

Advantageously according to the present invention, the composition prepared by using the oil from seeds of members of the gourd family is intended for the treatment of pathological conditions and/or disorders of the skin, associated with a congenital or acquired exaggeration of 5α-reductase activity.

Even more advantageously according to the present invention, the composition is intended for the treatment of prostatic hypertrophy, prostatic adenoma, acne, hyperseborrhea, alopecia or hirsutism.

The composition used according to the present invention may be a cosmetic, pharmaceutical, dermatological or nutritional food composition.

In a particular embodiment according to the present invention, the composition is a pharmaceutical or dermatological composition. Unlike the methods of cosmetic treatment according to the present invention according to which the hyperseborrhea, the alopecia or else the hirsutism are not of pathological origin and manifest themselves through esthetically bothersome phenomena on the skin and/or the hair, the therapeutic use of the oil according to the present invention makes it possible to treat forms of acne, of hyperseborrhea, of alopecia or of hirsutism which exhibit a pathological nature.

A subject of the present invention is also the use of at least one oil from seeds from members of the gourd family chosen from the group consisting of *Lagenaria, Luffa* and *Momordica*, advantageously *Lagenaria leucaritha, Luffa acutangula, Luffa cylindrica* and *Momordica charantia*, for preparing a composition, advantageously a pharmaceutical or dermatological composition, intended for the treatment of prostatic hypertrophy, prostatic adenoma, acne, hyperseborrhea, alopecia or hirsutism.

A subject of the present invention is also a method of cosmetic treatment, characterized in that at least one oil from seeds from members of the gourd family chosen from the group consisting of *Lagenaria, Luffa* and *Momordica*, advantageously *Lagenaria leucaritha, Luffa acutangula, Luffa cylindrica* and *Momordica charantia*, is applied to the skin, the mucous membranes, the nails or the hair in order to inhibit 5α-reductase activity.

Advantageously according to the method of cosmetic treatment of the present invention, the cosmetic composition is applied to greasy skin and/or to greasy hair, to shiny skin and/or to shiny hair, to skin exhibiting spots, blackheads or comedones, to greasy skin with a tendency toward acne, to greasy skin with blemishes, to areas of the scalp affected by alopecia or to areas of the skin which are very hairy.

In fact, according to the present invention, unlike hormonal medical treatments, the methods of cosmetic treatment of greasy and/or shiny skin or hair, of skin exhibiting spots, blackheads or comedones, of greasy skin with a tendency toward acne or with blemishes, of areas of the scalp affected by alopecia or of areas of the skin which are very hairy make it possible to improve the person's appearance by visibly reducing the unsightly and esthetically bothersome phenomena associated with hyperseborrhea, which in particular give the skin and/or the hair a greasy and/or shiny appearance and which can cause the appearance of spots, comedones or blackheads, with alopecia, which manifests itself through loss of hair or of body hair, and with hirsutism, which manifests itself through areas which are very hairy. These are cases where the hyperseborrhea, the alopecia or else the hirsutism are not of pathological origin, but originate, for example in the case of alopecia, from external attacking factors (bleaching, dyeing) or else from aging.

Finally, a subject of the present invention is the use of at least one oil from the seeds of members of the gourd family chosen from the group consisting of *Lagenaria, Luffa* and *Momordica*, advantageously *Lagenaria leucaritha, Luffa acutangula, Luffa cylindrica* and *Momordica charantia*, in a nutritional food composition or a foodstuff for humans and/or animals as an additive for inhibiting 5α-reductase activity.

According to an advantageous embodiment of the use according to the present invention, the oil from seeds of members of the gourd family is extracted according to the process consisting in extracting the total lipids from seeds from members of the gourd family, dried and ground beforehand, using a solvent for the oils, advantageously by soxhlet extraction, and then in evaporating off said solvent, or according to the process consisting in extracting the lipids from seeds of members of the gourd family by mechanical pressing of the seeds under cold conditions, advantageously by means of a continuous screw press, so as to produce, after filtration, first-press virgin oils.

According to another advantageous embodiment of the use according to the present invention, the oil extracted from seeds of members of the gourd family is used according to a proportion of between 0.01 and 95%, preferably between 0.1 and 30% by weight, relative to the total weight of the composition.

The following examples are given in a nonlimiting capacity and illustrate the present invention.

Unless otherwise specified, the percentages indicated in the following examples are percentages by weight. In the following examples, all the oils from seeds of members of the gourd family were extracted with hexane, starting with an amount of approximately 500 g of seeds of members of the gourd family.

| Example 1: Composition of the oil extracted from seeds of members of the gourd family | | | |
|---|---|---|---|
| Analytical data | Bottle gourd | "Pitted" gourd | Long gourd |
| Example 1.1: Composition of the oil extracted from seeds of bottle, "pitted" and long gourds (*Lagenaria leucaritha*) | | | |
| Characteristics | Light yellow-colored fluid oil | Light yellow-colored fluid oil | Light yellow-colored fluid oil |
| Acid index (mg KOH/g) | <10 | <10 | <10 |
| Fatty acid distribution (%) | | | |
| Palmitic acid | 12–18 | 10–18 | 12–20 |
| Stearic acid | 3–8 | 4–8 | 4–9 |
| Oleic acid | 4–9 | 4–8 | 12–30 |
| Linoleic acid | 65–75 | 65–75 | 35–60 |
| Unsaponifiable (%) | <1.5 | <1.5 | <1.5 |
| Analytical data | Angled luffa | Smooth luffa | Balsam pear |
| Example 1.2: Composition of the oil extracted from seeds of smooth luffa (*Luffa cylindrica*) and angled luffa (*Luffa acutangula*) and from balsam pear (*Momordica charantia*) | | | |
| Characteristics | Dark green-colored fluid oil | Dark green-colored fluid oil | Beige-colored solid oil (butter) |
| Acid index (mg KOH/g) | <10 | <10 | <10 |
| Fatty acid distribution (%) | | | |
| Palmitic acid | 20–25 | 15–25 | 0.5–5 |
| Stearic acid | 3–7 | 6–12 | 25–35 |
| Oleic acid | 6–11 | 11–20 | 1–5 |
| Linoleic acid | 52–63 | 50–60 | 9–16 |
| Conjugated tri-unsaturated acids | — | — | 45–65 (1) |
| Unsaponifiable (%) | <2 | <2 | <2 |

(1) mixture of punicic acid (<3%), α-eleostearic acid (<65%) and β-eleostearic acid (<3%)

Example 2: Cosmetic compositions

Example 2.1: Cream for skin with a tendency toward acne No. 1

| | % by weight |
|---|---|
| Water | qs 100 |
| Isononyl isononanoate | 7 |
| di(C$_{12-13}$ Alkyl) malate | 7 |
| Isocetyl stearate | 5 |
| Butylene glycol | 3 |
| *Oriza Sativa* | 2.5 |
| Balsam pear oil | 0.1 to 30 |
| Dicaprylyl ether | 2 |
| Silanediol salicylate | 2 |
| Arachidyl alcohol | 1.6 |
| Tromethamine | 1.2 |
| Cetyl alcohol | 1 |
| Salicylic acid | 1 |
| Ascorbyl glucoside | 1 |
| Glycine | 1 |
| Tocopherol acetate | 1 |
| Behenyl alcohol | 0.9 |
| Squalane | 0.8 |
| Sodium citrate | 0.7 |
| Copolymer PPG-12/SMDI | 0.5 |
| Arachidyl glucoside | 0.4 |
| Fragrance | 0.4 |
| Sclerotium gum | 0.2 |
| Cetearyl alcohol | 0.1 |
| Citric acid | 0.1 |
| Sepigel 305* | 0.1 |
| Preserving system | qs |

*product sold by the company Seppic

Example 2.2: Cream for skin with a tendency toward acne No. 2

| | |
|---|---|
| Water | qs 100 |
| Isononyl isononanoate | 7 |
| di(C$_{12-13}$ Alkyl) malate | 7 |
| Isocetyl stearate | 5 |
| Butylene glycol | 3 |
| *Oriza Sativa* | 2.5 |
| Smooth luffa oil | 0.1 to 30 |
| Dicaprylyl ether | 2 |
| Silanediol salicylate | 2 |
| Arachidyl alcohol | 1.6 |
| Tromethamine | 1.2 |
| Cetyl alcohol | 1 |
| Salicylic acid | 1 |
| Ascorbyl glucoside | 1 |
| Glycine | 1 |
| Tocopherol acetate | 1 |
| Behenyl alcohol | 0.9 |
| Squalane | 0.8 |
| Sodium citrate | 0.7 |
| Copolymer PPG-12/SMDI | 0.5 |
| Arachidyl glucoside | 0.4 |
| Fragrance | 0.4 |
| Sclerotium gum | 0.2 |
| Cetearyl alcohol | 0.1 |
| Citric acid | 0.1 |
| Sepigel 305* | 0.1 |
| Preserving system | qs |

*product sold by the company Seppic

Example 2.3: Cream for skin with a tendency toward acne No. 3

| | |
|---|---|
| Water | qs 100 |
| Isononyl isononanoate | 7 |
| di(C$_{12-13}$ Alkyl) malate | 7 |
| Isocetyl stearate | 5 |
| Butylene glycol | 3 |
| *Oriza Sativa* | 2.5 |
| Bottle gourd oil | 0.1 to 30 |
| Dicaprylyl ether | 2 |
| Silanediol salicylate | 2 |
| Arachidyl alcohol | 1.6 |
| Tromethamine | 1.2 |
| Cetyl alcohol | 1 |
| Salicylic acid | 1 |
| Ascorbyl glucoside | 1 |
| Glycine | 1 |
| Tocopherol acetate | 1 |
| Behenyl alcohol | 0.9 |
| Squalane | 0.8 |
| Sodium citrate | 0.7 |
| Copolymer PPG-12/SMDI | 0.5 |
| Arachidyl glucoside | 0.4 |
| Fragrance | 0.4 |
| Sclerotium gum | 0.2 |
| Cetearyl alcohol | 0.1 |
| Citric acid | 0.1 |
| Sepigel 305* | 0.1 |
| Preserving system | qs |

*product sold by the company Seppic

Example 2.4: Foaming washing emulsion for skin with a tendency toward acne No. 1

| | |
|---|---|
| Water | qs 100 |
| Arlatone duo* | 20 |
| Coconut glucoside | 12 |
| Hydroxypropyl guar | 2 |
| Balsam pear oil | 0.1 to 30 |
| PEG-200 hydrogenated glyceryl palmate | 1.1 |
| PEG-7 glyceryl cocoate | 1.1 |
| Silanediol salicylate | 1 |
| Cocamide DEA | 1 |
| Caprylyol glycine | 0.5 |
| Potassium sorbate | 0.5 |
| Polyquaternium 10 | 0.4 |
| Fragrance | 0.4 |
| Citric acid | 0.3 |
| Zinc PCA | 0.2 |

*product sold by the company Quimasso

Example 2.5: Foaming washing emulsion for skin with a tendency toward acne No. 2

| | |
|---|---|
| Water | qs 100 |
| Arlatone duo* | 20 |
| Coconut glucoside | 12 |
| Hydroxypropyl guar | 2 |
| Long gourd oil | 0.1 to 30 |
| PEG-200 hydrogenated glyceryl palmate | 1.1 |
| PEG-7 glyceryl cocoate | 1.1 |
| Silanediol salicylate | 1 |
| Cocamide DEA | 1 |
| Caprylyol glycine | 0.5 |
| Potassium sorbate | 0.5 |
| Polyquaternium 10 | 0.4 |
| Fragrance | 0.4 |
| Citric acid | 0.3 |
| Zinc PCA | 0.2 |

*product sold by the company Quimasso

Example 2.6: Foaming washing emulsion for skin with a tendency toward acne No. 3

| | |
|---|---|
| Water | qs 100 |
| Arlatone duo* | 20 |
| Coconut glucoside | 12 |
| Hydroxypropyl guar | 2 |
| Angled luffa oil | 0.1 to 30 |
| PEG-200 hydrogenated glyceryl palmate | 1.1 |
| PEG-7 glyceryl cocoate | 1.1 |
| Silanediol salicylate | 1 |
| Cocamide DEA | 1 |
| Caprylyol glycine | 0.5 |
| Potassium sorbate | 0.5 |
| Polyquaternium 10 | 0.4 |
| Fragrance | 0.4 |
| Citric acid | 0.3 |
| Zinc PCA | 0.2 |

*product sold by the company Quimasso

Example 2.7: Matting emulsion No. 1

| | |
|---|---|
| Water | qs 100 |
| di(C$_{12-13}$ Alkyl) malate | 10 |

-continued

| | |
|---|---|
| Glycerol | 5 |
| *Oryza Sativa* | 4 |
| Balsam pear oil | 0.1 to 30 |
| PEG-5 glyceryl stearate | 3.5 |
| Sepigel* | 2.5 |
| Butylene glycol | 2.4 |
| Silanediol salicylate | 2 |
| Glyceryl stearate | 1.5 |
| Ceresin | 1.5 |
| PEG-40 stearate | 1.5 |
| Sorbitan stearate | 1 |
| Nylon-6 | 1 |
| Zinc PCA | 1 |
| Cetyl alcohol | 1 |
| Caprylyl glycol | 0.6 |
| Fragrance | 0.5 |
| Piroctone Olamine | 0.3 |
| Pyridoxine HCl | 0.2 |
| Tocopherol | 0.2 |

*product sold by the company Seppic

Example 2.8: Matting emulsion No. 2

| | |
|---|---|
| Water | qs 100 |
| di($C_{12-13}$ Alkyl) malate | 10 |
| Glycerol | 5 |
| *Oryza Sativa* | 4 |
| Smooth luffa oil | 0.1 to 30 |
| PEG-5 glyceryl stearate | 3.5 |
| Sepigel* | 2.5 |
| Butylene glycol | 2.4 |
| Silanediol salicylate | 2 |
| Glyceryl stearate | 1.5 |
| Ceresin | 1.5 |
| PEG-40 stearate | 1.5 |
| Sorbitan stearate | 1 |
| Nylon-6 | 1 |
| Zinc PCA | 1 |
| Cetyl alcohol | 1 |
| Caprylyl glycol | 0.6 |
| Fragrance | 0.5 |
| Piroctone Olamine | 0.3 |
| Pyridoxine HCl | 0.2 |
| Tocopherol | 0.2 |

*product sold by the company Seppic

Example 2.9: Matting emulsion No. 3

| | |
|---|---|
| Water | qs 100 |
| di($C_{12-13}$ Alkyl) malate | 10 |
| Glycerol | 5 |
| *Oryza Sativa* | 4 |
| Bottle gourd oil | 0.1 to 30 |
| PEG-5 glyceryl stearate | 3.5 |
| Sepigel* | 2.5 |
| Butylene glycol | 2.4 |
| Silanediol salicylate | 2 |
| Glyceryl stearate | 1.5 |
| Ceresin | 1.5 |
| PEG-40 stearate | 1.5 |
| Sorbitan stearate | 1 |
| Nylon-6 | 1 |
| Zinc PCA | 1 |
| Cetyl alcohol | 1 |
| Caprylyl glycol | 0.6 |
| Fragrance | 0.5 |
| Piroctone Olamine | 0.3 |
| Pyridoxine HCl | 0.2 |
| Tocopherol | 0.2 |

*product sold by the company Seppic

Example 2.10: Tinted matting emulsion No. 1

| | |
|---|---|
| Water | qs 100 |
| di($C_{12-13}$ Alkyl) malate | 10 |
| Glycerol | 5 |
| *Oryza Sativa* | 4 |
| Balsam pear oil | 0.1 to 30 |
| PEG-5 glyceryl stearate | 3.5 |
| Sepigel* | 2.5 |
| Butylene glycol | 2.4 |
| Silanediol salicylate | 2 |
| Glyceryl stearate | 1.5 |
| Ceresin | 1.5 |
| PEG-40 stearate | 1.5 |
| Sorbitan stearate | 1 |
| Nylon-6 | 1 |
| Zinc PCA | 1 |
| Cetyl alcohol | 1 |
| Caprylyl glycol | 0.6 |
| Fragrance | 0.5 |
| Brown iron oxide | 0.3 |
| Piroctone Olamine | 0.3 |
| Pyridoxine HCl | 0.2 |
| Iron oxide | 0.1 |
| Tocopherol | 0.2 |
| Black iron oxide | 0.1 |

*product sold by the company Seppic

Example 2.11: Tinted, matting emulsion No. 2

| | |
|---|---|
| Water | qs 100 |
| di($C_{12-13}$ Alkyl) malate | 10 |
| Glycerol | 5 |
| *Oryza Sativa* | 4 |
| Bottle gourd oil | 0.1 to 30 |
| PEG-5 glyceryl stearate | 3.5 |
| Sepigel* | 2.5 |
| Butylene glycol | 2.4 |
| Silanediol salicylate | 2 |
| Glyceryl stearate | 1.5 |
| Ceresin | 1.5 |
| PEG-40 stearate | 1.5 |
| Sorbitan stearate | 1 |
| Nylon-6 | 1 |
| Zinc PCA | 1 |
| Cetyl alcohol | 1 |
| Caprylyl glycol | 0.6 |
| Fragrance | 0.5 |
| Brown iron oxide | 0.3 |
| Piroctone Olamine | 0.3 |
| Pyridoxine HCl | 0.2 |
| Iron oxide | 0.1 |
| Tocopherol | 0.2 |
| Black iron oxide | 0.1 |

*product sold by the company Seppic

Example 2.12: Shampoo No. 1

| | |
|---|---|
| Water | qs 100 |
| Sodium lauroamphoacetate | 11 |
| Coconut glucoside | 11 |
| Magnesium laureth sulfate | 6 |
| Balsam pear oil | 0.1 to 30 |
| PEG-40 glyceryl cocoate | 2.4 |
| PEG-150 distearate | 1.2 |
| Sodium coceth sulfate | 1.1 |
| Salicylic acid | 1 |
| Disodium EDTA | 0.3 |
| Fragrance | 0.2 |
| Sodium hydroxide | qs pH = 6.5 |
| Preserving system | qs |

Example 2.13: Shampoo No. 2

| | |
|---|---|
| Water | qs 100 |
| Sodium lauroamphoacetate | 11 |
| Coconut glucoside | 11 |
| Magnesium laureth sulfate | 6 |
| Long gourd oil | 0.1 to 30 |
| PEG-40 glyceryl cocoate | 2.4 |
| PEG-150 distearate | 1.2 |
| Sodium coceth sulfate | 1.1 |
| Salicylic acid | 1 |
| Disodium EDTA | 0.3 |
| Fragrance | 0.2 |
| Sodium hydroxide | qs pH = 6.5 |
| Preserving system | qs |

Example 2.14: Shampoo No. 3

| | |
|---|---|
| Water | qs 100 |
| Sodium lauroamphoacetate | 11 |
| Coconut glucoside | 11 |
| Magnesium laureth sulfate | 6 |

| | |
|---|---|
| -continued | |
| Angled luffa oil | 0.1 to 30 |
| PEG-40 glyceryl cocoate | 2.4 |
| PEG-150 distearate | 1.2 |
| Sodium coceth sulfate | 1.1 |
| Salicylic acid | 1 |
| Disodium EDTA | 0.3 |
| Fragrance | 0.2 |
| Sodium hydroxide | qs pH = 6.5 |
| Preserving system | qs |

Example 3

In vitro evaluation of the 5α-reductase activity of the balsam pear oil on the conversion of testosterone to 5α-dihydrotestosterone in normal human dermal fibroblast cultures Abbreviations used in the following examples:

EtOH: ethanol
DMSO: dimethyl sulfoxide
M199: name given to a standard culture medium
FCM: fibroblast culture medium
MEM: name given to the culture medium Minimum Essential Medium
FIM: fibroblast incubation medium
Rf: relative retention factor
FCS: fetal calf serum
5α-DHT: 5α-dihydrotestosterone It is proposed to evaluate the effect of the solid oil (butter) extracted from seeds of balsam pear (*Momordica charantia*), extracted with solvent (hexane), on 5α-reductase activity. An in vitro model of normal human dermal fibroblast cultures was selected.

1. Materials and Methods 1.1 Test Product, Reference Product, and Reagents

The balsam pear oil was provided by the Laboratoires Pharmascience and was stored at +4° C. until the time it was used. The effects of the test product were compared with those obtained in the presence of finasteride, used as reference product (finasteride, principle active agent of the tablets CHIBRO-PROSCAR: MERCK SHARP & DOHME CHIBRET).

The radioactive testosterone (labeled with tritium at positions 1, 2, 6 and 7, specific activity 95 Ci/mmol) was provided by AMERSHAM, the nonradiolabeled testosterone was provided by SIGMA.

The analytical quality reagents came from SIGMA, MERCK, BDH, ALDRICH or CARLO ERBA, unless otherwise indicated.

1.2 Test System

The fibroblast culture medium (FCM) consisted of MEM/M199 (3:1, v/v) supplemented with penicillin (50 IU/ml), streptomycin (50 pg/ml), sodium bicarbonate (0.2%, w/v) and FCS (10%, v/v).

The test system consisted of normal human dermal fibroblasts cultured in monolayer. The fibroblasts were isolated from a residue of an abdominoplasty carried out on a 30-year-old woman (subject No. i0006). The cells were used at the third passage; they were cultured, until the monolayers reached confluency, in the FCM medium at 37° C. in a humid atmosphere containing 5% $CO_2$.

1.3 Preparation of the Products and Incubation with the Test System

The fibroblast incubation medium (FIM) consisted of FCM supplemented with tritiated testosterone ($1.6×10^{-7}$ M, i.e. 6.32 µCi/ml) and nonradiolabeled testosterone ($3.84× 10^{-6}$ M).

The finasteride was extracted from the tablets by grinding, stirring in DMSO, centrifugation, and then collection of the supernatant (theoretical concentration of this solution: 1 mg/ml of finasteride), which was tested at 30 ng/ml. The balsam pear oil was solubilized at 2 mg/ml in the FCM medium containing 2.5% of ethanol, followed by dilution in the FCM medium in contact with the cells so as to obtain final concentrations of balsam pear oil of 5 and 10 µg/ml.

Time scale:

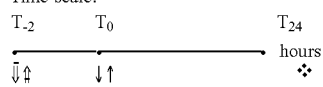

⇓: elimination of the FCM medium
⇑: preincubation of the test products and of the reference product prepared in the FCM medium
↓: elimination of the FCM media containing the test product or the reference product
↑: incubation of the test product and of the reference product prepared in the FIM medium
❖: determination of the 5α-reductase activity.

The fibroblast cultures were preincubated in the presence of the test product or of the reference product for 2 hours before addition of the substrate, the testosterone. For this step, the test product and the reference product were prepared in the FCM medium.

After preincubation, the fibroblast cultures were incubated in the presence of the test product or of the reference product prepared in the FIM medium, for 24 hours at 37° C. in a humid atmosphere containing 5% $CO_2$. Control cultures were incubated in the FIM medium in the absence of test product and of reference product.

Each experimental condition was tested in triplicate.

1.4 Evaluation of the Effects

After the incubation period, the cells were subjected to the action of ultrasound in the FIM medium. The cell lysates thus obtained were extracted with dichloromethane. After evaporation, the dry residues were taken up in methanol and were deposited onto silica $60F_{254}$ plates (MERCK, reference 5554).

Nonradiolabeled standards, testosterone, 5α-dihydro-testosterone and androstenedione, were deposited onto each of the plates.

The migration solvent was a mixture of dichloromethane and ether (7:3, v/v). At the end of migration, the silica plates were read using a BERTHOLD radioactivity scanner.

The nonradiolabeled standards were revealed by spraying 5% (v/v) sulfuric acid onto the chromatography plates which were then heated at 100° C. for 10 minutes.

Comparison of the Rf (relative retention factor) values determined for the standards with those obtained for the various radioactive metabolites made it possible to identify these metabolites.

The metabolization of the testosterone to 5α-dihydrotestosterone under the various experimental conditions was calculated; the results (areas of the 5α-dihydro-testosterone peaks counted by the BERTHOLD scanner) are expressed in pmol of 5α-DHT formed per pg of DNA. They have also been expressed as percentage of the 5α-reductase activity present in the "control cells" group. The total content of DNA was assayed using a fluorescent nuclear dye (Hoechst 33258) by fluorometry (excitation 356 nm, emission 458 nm).

1.5—Data Processing

The groups of data (control group and treated groups) were processed using a one factor analysis of variance (ANOVA 1, p<0.05), followed by a DUNNETT's test (p<0.05). The effect of the test product and of the reference product was compared with the "control cells" group.

2. Results and Discussion

The finasteride used as reference product and tested at 30 ng/ml inhibits the 5α-reductase activity by 70% (p<0.05). This result was expected and validates our test (table 2).

The balsam pear oil tested at 5 and 10 µg/ml inhibits the 5α-reductase activity by 39 and 50%, respectively (p<0.1 and p<0.05 respectively) (table 3).

3. Tables 3.1—Effect of finasteride on the 5α-reductase activity in normal human dermal fibroblast cultures after incubation for 24 hours

TABLE 2

|  | Control cells | Finasteride (30 ng/ml) |
|---|---|---|
| pmol of 5α-DHT/µg of DNA | 2.68 | 0.76 |
|  | 1.91 | 0.48 |
|  | 1.56 | 0.62 |
| Mean | 2.05 | 0.62** |
| Standard deviation | 0.57 | 0.14 |
| % control | 100 | 30 |

**mean statistically different from that of the control group (p < 0.05)

3.2—Effect of the balsam pear oil on the 5α-reductase activity in normal human dermal fibroblast cultures after incubation for 24 hours

TABLE 3

|  | Control cells | Balsam pear oil (5 µg/ml) | Balsam pear oil (10 µg/ml) |
|---|---|---|---|
| pmol of 5α-DHT/µg of DNA | 2.68 | 1.65 | 1.09 |
|  | 1.91 | 1.03 | 1.06 |
|  | 1.56 | 1.09 | 0.96 |
| Mean | 2.05 | 1.26* | 1.03** |
| Standard deviation | 0.57 | 0.34 | 0.07 |
| % control | 100 | 61 | 50 |

**mean statistically different from that of the control group (p < 0.05)
*mean statistically different from that of the control group (p < 0.1)

The invention claimed is:

1. A method for inhibiting 5α-reductase activity in a patient with greasy skin and/or greasy hair, skin exhibiting spots, blackheads or comedones, hyperseborrhea, acne, greasy skin with acne, greasy skin with blemishes, areas of the scalp affected by alopecia or areas of the skin affected by hirsutism, comprising administering to the patient a composition containing at least one oil extracted from seeds of members of the gourd family selected from the group consisting of *Lagenaria*, *Luffa* and *Momordica*.

2. The method as claimed in claim 1, wherein the composition inhibits 5α-reductase, the type 1 isoenzyme of 5α-reductase or type 2 isoenzyme of 5α-reductase.

3. A method as claimed in claim 1, wherein the members of the gourd family are chosen from *Lagenaria leucaritha*, *Luffa Acutangula*, *Luffa cylindrica* and *Momordica charantia*.

4. The method as claimed in claim 1, for administration in an external topical manner.

5. The method as claimed in claim 4, wherein the composition is applied to the skin, the mucous membranes, the nails or the hair.

6. The method as claimed in claim 1, wherein the composition is in the form of an aqueous, aqueous-alcoholic or oily solution, of an oil-in-water or water-in-oil or multiple emulsion, of an aqueous or oily gel, of an anhydrous liquid, pasty or solid product, or of a dispersion of oil in an aqueous phase by means of spherules.

7. The method as claimed in claim 1, wherein the oil from seeds of members of the gourd family can be obtained according to the process comprising drying and grinding seeds of members of the gourd family, extracting the lipids from the seeds, using a solvent for the oils, and then in evaporating off said solvent, or according to the process consisting in extracting the lipids from seeds of members of the gourd family by mechanical cold pressing of the seeds.

8. The method as claimed in claim 1, wherein the oil extracted from seeds of members of the gourd family is present at a concentration of between 0.01 and 95% by weight, relative to the total weight of the composition.

9. The method as claimed in claim 1, wherein the oil extracted from the seeds of members of the gourd family is present at a concentration of between 0.1 and 30% by weight, relative to the total weight of the composition.

10. The method as claimed in claim 1, wherein the patient has acne, hyperseborrhea, alopecia or hirsutism.

11. The method as claimed in claim 1, wherein the composition is a pharmaceutical, dermatological, cosmetic or food composition.

* * * * *